United States Patent [19]

Hill

[11] 4,349,976

[45] Sep. 21, 1982

[54] APPARATUS FOR LOCATING AN AQUATIC ENVIRONMENT WITH A PH PREFERRED BY LARGEMOUTH AND STRIPED BASS FISH

[76] Inventor: Loren G. Hill, 1125 Westbrooke Ter., Norman, Okla. 73069

[21] Appl. No.: 929,005

[22] Filed: Jul. 28, 1978

Related U.S. Application Data

[62] Division of Ser. No. 755,249, Dec. 29, 1976, Pat. No. 4,103,447.

[51] Int. Cl.$^3$ .............................................. A01K 97/00
[52] U.S. Cl. ...................................... 43/4; 73/170 A; 119/3
[58] Field of Search ............................ 43/4, 4.5, 17.1; 324/438; 119/2, 3; 73/170 A

[56] References Cited

U.S. PATENT DOCUMENTS

| 2,672,845 | 3/1954 | Schneithorst | 119/5 |
| 3,387,587 | 6/1968 | Kelley et al. | 119/2 |
| 3,540,023 | 11/1970 | Potoroka | 43/4 |
| 3,806,797 | 4/1974 | Harvey | 324/438 |
| 3,876,312 | 4/1975 | Harcrow | 43/4 |
| 3,934,197 | 1/1976 | Pettersen | 324/438 |
| 3,968,586 | 7/1976 | Peterson | 43/4.5 |
| 4,050,308 | 9/1977 | Lee | 73/170 A |

OTHER PUBLICATIONS

Davies, W. D.; "The Effects of Total Dissolved Solids . . . ", Progressive Fish Culturist, vol. 35, No. 3, pp. 157-160, Jul. 1973.
Best, G. A.; "The Continuous Monitoring of Water Quality, Public Health Engineer, No. 15, pp. 72-83, 1975.
Pegg, W. J. and Jenkins, C. R.; "Physiological Effects of Sublethal Levels of Acid Water on Fish", West Virginia Water Research Institute Bulletin 6, May 1976.
Undersea Technology, Sigalove et al., A Continuous Ocean Sampling and Analysis System, vol. 13, No. 3, Mar. 1972. pp. 24-27.
Heacox, Cecil, *Field & Stream*, "Fishing by Degrees", May 1959.

*Primary Examiner*—Stephen G. Kunin
*Assistant Examiner*—K. Bradford Adolphson
*Attorney, Agent, or Firm*—William R. Laney

[57] ABSTRACT

Apparatus and methods for locating and catching certain fish species known as Largemouth Bass and Striped Bass, by locating those zones within a body of fresh water having a pH within the range of from about pH 7.5 to about pH 8.0, followed by fishing for these species in those zones. The invention further includes, as another of its aspects, the raising of the same species of fish by maintaining the pH of a selected aquatic environment within said pH range during the growth of the fish.

2 Claims, 8 Drawing Figures

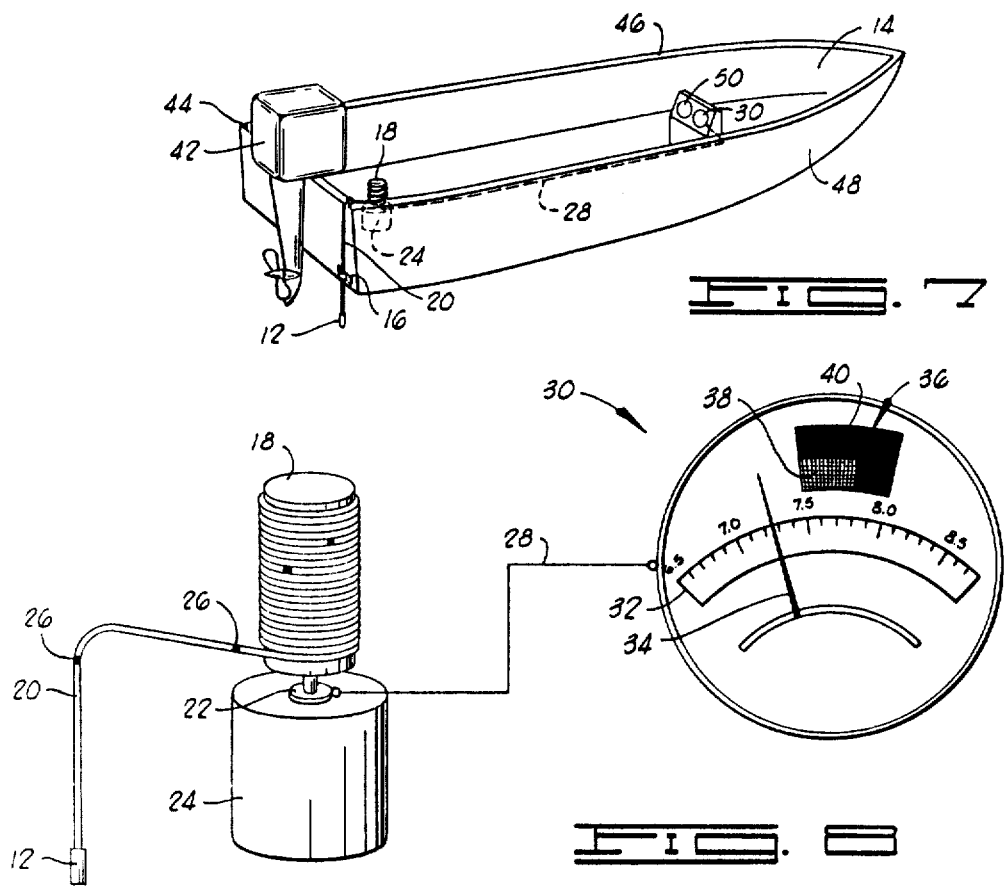

APPARATUS FOR LOCATING AN AQUATIC ENVIRONMENT WITH A PH PREFERRED BY LARGEMOUTH AND STRIPED BASS FISH

This is a division of application Ser. No. 755,249, filed Dec. 29, 1976, now U.S. Pat. No. 4,103,447.

BACKGROUND OF THE INVENTION

1. Field of the Invention

This invention relates to apparatus and methods for locating, catching and raising certain freshwater aquatic organisms, and more particularly, but not by way of limitation, to methods of locating, catching and raising certain species of fish.

2. Description of the Prior Art

Certain environmental parameters are known to exert influence upon aquatic organisms. The influence of a given parameter is different upon different species of aquatic organisms. For a given environmental parameter and a given species of organism, the influence of that parameter on the species can be described by two concepts. These concepts are requirements and tolerances. The concept of requirements relates to the necessary range of the given parameter for the viability of the species in metabolism, growth and reproduction. The concept of tolerances relates to the extreme limits of the given parameter in which the species can live, but in which the species cannot survive indefinitely and cannot grow or reproduce.

Three environmental parameters which have heretofore been recognized as influencing the behavior of certain gilled aquatic organisms are salinity, dissolved oxygen concentration and temperature. Salinity, as used in this context, is the concentration of dissolved solids present in the water and is expressed in parts per million (ppm). Dissolved oxygen concentration is also expressed in parts per million.

More particularly, these three parameters have been found to behaviorally influence certain species of fish. For example, most pelagic fish—fish which are for the most part active free swimmers, such as shad, white bass and striped bass—are organisms which require a considerable amount of oxygen—around 8 ppm—to maintain an active metabolism. That is, they require dissolved oxygen concentrations of that level to be physically active and to grow and reproduce. However, they can tolerate dissolved oxygen concentrations of 6 ppm and below, though they cannot grow and reproduce at such low oxygen concentrations.

The presence or absence and the nature of physical structure (tree limbs and the like) in the water is known to be another environmental parameter influencing the behavior of fish.

The reasons for which a given species of fish requires and seeks out an environment having certain values of these parameters are not precisely known, but it is known that in the case of oxygen, salinity and temperature, the reasons have to do with the metabolism and body chemistry of the species. The species does not possess the capacity to regulate its body temperature and chemistry independent of its environment, but it can sense the presence of favorable or unfavorable environmental conditions, and can and does seek out an environment with favorable conditions to permit it to maintain its metabolism and body chemistry at the levels required for viability. For example, fish are cold-blooded—that is, their body temperature is dependent upon the temperature of their environment. Fish therefore tend to seek out an environment with water temperature near their preferred body temperature. The most desirable temperature for bass, for example, is from 65° F. to 75° F.

This tendency of certain species of fish to seek out an environment having preferred values of salinity, temperature and dissolved oxygen concentration has been previously recognized by icthyologists, and has been the basis of apparatus and methods for locating, catching and raising fish.

In the commercial raising of certain aquatic organisms, including fish, it has been recognized that the growth rate and general health of the organisms can be enhanced by maintaining the preferred values of one or more of these environmental parameters.

The location and catching of aquatic organisms from their natural environment have long been achieved by methods based in large part upon first locating those areas of the environment most attractive to the organisms, and in more recent methods, having the values of the aforementioned parameters which have been found to be preferred by the particular species of organism being sought.

In particular, very significant commercial success has been realized by manufacturers of apparatus suitable for determining the dissolved oxygen concentration and the temperature of the water in forms suitable for sale to, and use by, sportsmen in quest of various species of freshwater game fish. However, such devices and methods have not been entirely successful. Often fish have been found, for example, in areas of relatively low dissolved oxygen concentration, even though their metabolic demand is not thereby optimally satisfied. Sometimes they have been found in areas of temperature or salinity with values of those parameters very much different from what are known to be the preferred values for the species being observed. Occasionally, a given species has been found in an environment in which values of all three of the aforementioned parameters are very much different from its preferred values, and sometimes a species has been observed to actually avoid areas having desirable values of all three parameters and instead to inhabit areas with less desirable temperature, salinity and dissolved oxygen concentration.

SUMMARY OF THE INVENTION

Observation of these heretofore unexplainable occasional behavior patterns led me to surmise that there must exist one or more additional influential environmental parameters, and that moreover one or more of these unknown parameters must have an effect which overrides even the combined effects of the three aforementioned parameters.

I have discovered that this previously unknown parameter is the hydrogen ion concentration within the water and, based on this discovery, I have conceived and developed apparatus and methods for locating, catching and raising fish, these methods and apparatus being more successful than those known to the prior art.

The hydrogen ion concentration is usually presented as the pH. The pH is defined as the logarithm to the base ten of the reciprocal of the hydrogen ion concentration, where the hydrogen ion concentration is expressed in moles per liter. The pH scale ranges from pH 0 to pH 14, with a pH 7 as the neutral point where there is an equal concentration of hydrogen ions and hydroxyl ions. As the pH increases above pH 7, the concentration of hydroxyl ions increases and the water is said to be increasingly basic. As the pH decreases below pH 7, the concentration of hydrogen ions increases and the water is said to be increasingly acidic.

I have discovered that certain species of fish have a marked preference for an environment having a pH within a very narrow band. This preferred pH band varies significantly from species to species.

It has also been discovered that pH is an environmental parameter which is of equal or greater criticality than either salinity, dissolved oxygen concentration or temperature. Moreover, it has been discovered that certain fish species, when given a choice between a first environment having desirable pH but undesirable salinity, dissolved oxygen concentration and temperature, and a second environment having an undesirable pH but a desirable salinity, dissolved oxygen concentration and temperature, will choose to inhabit the first environment.

More particularly, certain species of freshwater game fish, namely bass, have been found to exhibit a marked preference for a slightly basic or alkaline environment. That is, they require an environment with a pH slightly above pH 7. Even among different species of bass, however, the preferred pH is different, and each species consistently seeks out an environment with a pH value within a relatively narrow range. The *Micropterus salmoides,* commonly known as the Largemouth Bass, can tolerate a pH as low as pH 6.5 and as high as pH 9.6, but prefers an environment within the range of pH 7.5 to pH 7.8. The *Morone saxatilis,* commonly known as the Striped Bass, has approximately the same range of tolerable pH, but its narrower range of preferred pH is from pH 7.5 to pH 8.0, which is slightly more alkaline than the preferred range of the Largemouth Bass.

The natural habitats of these fish are freshwater lakes, ponds, rivers and streams. At any given time, the pH at the surface of a body of water may vary widely over relatively short distances. At any given position within a body of water, the pH may vary widely over relatively short time spans. The pH may also vary with depth below a given point on the surface of a body of water. These changes in pH are associated primarily with photosynthesis by aquatic plants, and to a lesser extent with the minerology of the terrain from which feeder streams originate.

Based on this preference of certain species of aquatic organisms for an environment having a pH within a relatively narrow range, and upon the widely varying pH conditions present within the natural habitats of these species, I have devised apparatus and methods for locating and catching such pH-responsive species. Based on the enhanced growth and viability of a species when subjected to a controlled environment having a pH within the preferred range of that species, I have devised improved methods of raising said species.

The apparatus of the present invention for locating and catching freshwater aquatic organisms, and particularly certain fish species, are comprised of pH sensing devices, pH recording devices, means for connecting the sensing and recording devices, means for transporting the devices upon or within a body of water, and means for indicating, in simplistic and easily understood fashion, when the pH of the water is within a predetermined preferred range for habitation by a given species of aquatic organism.

The methods of the present invention for locating aquatic organisms within their natural habitat require, first, that the desired pH range of the aquatic organism being sought be determined. Then a pH sensing device must be transported to a plurality of locations within a body of water. The pH sensing device is placed in contact with the body of water and the pH of the water is measured. The pH values measured are then compared to the preferred pH range for the species being sought. Organisms of the desired species will usually be found in those zones of the body of water having a pH nearest the preferred pH range for that species if external influences have not recently occurred to cause the organisms to disperse to less optimum, though tolerable, pH environments.

The methods of the present invention for catching aquatic organisms are comprised of placing appropriate tackle for catching the desired species within those zones of the body of water with the most desirable pH as found by the abovedescribed methods of locating the aquatic organisms.

The methods of the present invention for raising certain freshwater fish are comprised of maintaining the pH of the environment within the preferred range for the species being raised.

It is, therefore, a broad, general object of the present invention to provide improved methods for locating, catching and raising aquatic organisms, and more particularly certain species of fish.

A further object of the present invention is the provision of apparatus for use in carrying out these improved methods of locating and catching aquatic organisms, and particularly certain species of freshwater fish.

Another, more specific object of the present invention is the provision of an improved method for locating certain species of freshwater game fish by first locating those parts of a body of water having the preferred pH of the species being sought.

Yet another object of the present invention is the provision of an improved method of locating and catching the *Micropterus salmoides,* commonly known as the Largemouth Bass, whereby a fisherman first locates those areas of a body of water having a pH in or near the range of pH 7.5 to pH 7.8.

Other and further objects, features and advantages of the present invention will be readily apparent to those skilled in the art upon a reading of the description of preferred embodiments which follows when taken in conjunction with the accompanying drawings.

BRIEF DESCRIPTION OF THE DRAWINGS

FIGS. 1–6 are graphical and tabular representations of experiments I have conducted to determine the preferred values of certain water parameters for certain freshwater aquatic organisms and to determine which of those parameters is the most influential upon the migratory tendencies of said aquatic organisms.

FIG. 7 is a perspective view of a preferred embodiment of the apparatus of the present invention.

FIG. 8 is a view of the pH sensing device, the pH display meter and the electrical circuit connecting them, all constituting components of the apparatus of the invention.

DETAILED DESCRIPTION OF PREFERRED EMBODIMENTS OF THE INVENTION

Figure 2:
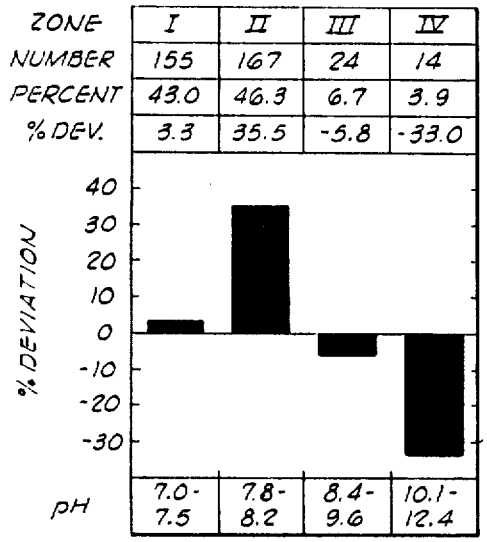

As previously indicated herein, observations that, from time to time, fish are found at locations in freshwater bodies which are characterized by less than optimum dissolved oxygen, or temperature, or salinity (or all of these parameters) led to the conclusion that some other water parameter must be strongly influential with respect to the behavior of fish—apparently even perhaps of supervening or overriding importance with respect to the commonly observed and examined parameters of dissolved oxygen, temperature and salinity. For the purpose of investigating one water parameter which I have conceived as possibly being that of major influence, though not previously recognized as such, I have conducted a number of laboratory and field experiments. The object of these experiments has been to observe and investigate the effect upon the behavior of fish of the relative acidity or basicity of the water constituting the natural habitat of freshwater game fish, and to compare the effect of pH upon the behavior of fish with the stimuli constituted by the other water parameters hereinbefore described.

Because within my own personal observations, the apparently anomalous behavior described had been observed to be characteristic of Striped Bass and Largemouth Bass and also because these fish species constitute a favorite of sports fishermen, my experiments have been initially carried out with respect to these species. In carrying out the laboratory experiments, a relatively large number of specimens constituting fingerlings of about six months age were placed in a controlled aquatic environment. By a "relatively large number" is meant a number large enough to give statistically significant results considering the methodology employed. To the extent possible, the specimens selected were as nearly physically identical as possible so that any effects of physical domination of weaker specimens by larger, stronger and more aggressive specimens was minimized.

In establishing the aquatic environment in which the experiments were carried out, a body of water was divided into a plurality of parametrically discrete yet aquatically communicating zones so that the several specimens were individually located in, and identifiable with, one zone or another at any given time, and were subject to controlled water parameter values therein, but were free to swim from one zone to another.

The environmental parameters of pH, salinity, dissolved oxygen and temperature were initially established uniformly throughout the entire controlled aquatic environment, that is, the value of those parameters were established as the same in all of the several discrete zones. The values used were pH 7.0, salinity 1300 ppm, dissolved oxygen 8 ppm and temperature 70° F. This was done as a control test to determine which zones, if any, were preferred by the species when the four environmental parameters listed above were constant throughout the test environment. Such control also afforded observation of any effects which anomalies of structure used in the establishment of the zones, differences in light, etc., might have upon the specimens independent of any variation in the several specifically investigated parameters. During the control test, the number of control specimens within each zone was counted and recorded.

Next a gradient in one of the four parameters was created throughout the environment and the other three parameters were held constant. This is to say that in the several parametrically discrete zones, one of the four parameters was caused to vary in value, with a different value for that parameter being existent in each of the several discrete zones. After allowing sufficient time (one hour) for the environmental influence of the varied parameter to evoke response in the specimens observed, the number of specimens within each of the parametrically discrete zones was counted and recorded. Concurrently with the time of counting of the specimens, the range of values of the varied parameter within each of the zones was measured and recorded. The number of specimens within each zone was then compared to the number of specimens which were within that zone during the control test. If the number of specimens increased, the inference was that a preferred range of the varied parameter was the range which was measured for that particular zone—that is, the specimens of bass investigated appeared to prefer the environment within that particular zone to those in the other zones. This procedure was then repeated and the results of numerous tests were combined and then compared in order to determine the most preferred ranges of the varied parameters for the bass species being studied.

The results of the control test for the Largemouth Bass showed approximately 39.7% of the specimens were located in Zone I, 10.8% in Zone II, 12.5% in Zone III, and 36.9% in Zone IV. The tendency of the specimens to congregate in larger numbers in Zones I and IV is believed to be due to the presence in those zones of some zone-defining boundary structure which was not present in, or characteristic of, Zones II and III.

FIGS. 1–6 are all interpreted in the following manner. The first line, labeled "Zone," indicates the four discrete zones of the test chamber. The second line, labeled "Number," is the number of specimens which were located in each of the four discrete zones. The third line, labeled "Percent," is the percent of the total number of specimens which were located in each of the four discrete zones. The fourth line, labeled "% Dev.," is the percent deviation from the control test; e.g., in FIG. 1, the percent of specimens in Zone I was 3.6% of the total, the control test showed 39.7% of the specimens in Zone I. Therefore, the "% Dev."=3.-6%−39.7%=−36.1%. Below the "% Dev." data is a graphical representation of the same, labeled "% Deviation." The line or lines below that graphical representation represent the values of the varied parameters within each of the four zones for the particular test, e.g., in FIG. 1 the only parameter which was varied was "Dissolved $O_2$", and the value of "Dissolved $O_2$" in Zone I varied from 3.6 to 4.2 ppm. The other parameters were maintained at the values used in the control test.

Figure 1:
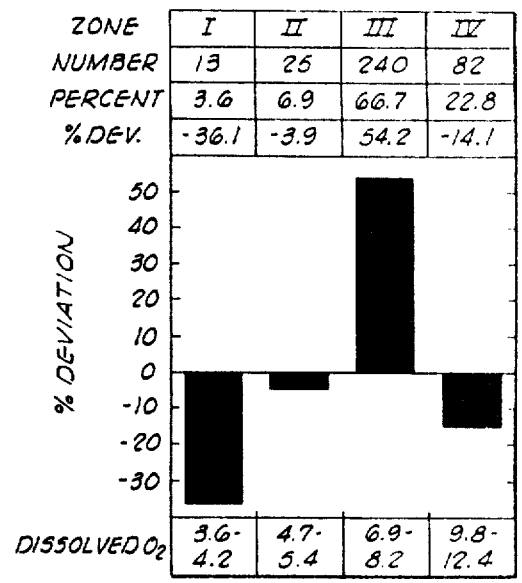
Figure 4:
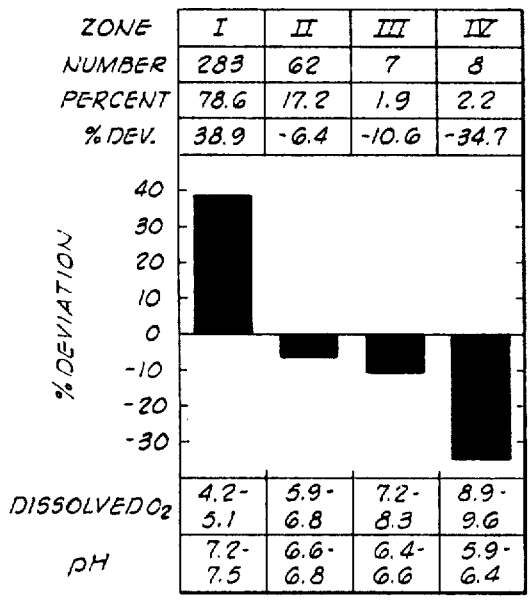

In FIG. 1 of the drawings, the effect of varying the dissolved oxygen content as between four parametrically discrete zones has been set forth in graphic form. This test utilized the *Micropterus salmoides* (Largemouth Bass). Results clearly show a preference of the bass specimens utilized for a dissolved oxygen content in the range of 6.9 ppm to 8.2 ppm.

In another test utilizing the *Micropterus salmoides* species, the pH was varied in the four parametrically discrete zones while maintaining the oxygen content, the temperature and the dissolved solids at constant control test levels throughout the four zones. The results of this test are set forth graphically in FIG. 2. From such results, it will be perceived that the Largemouth Bass indicated a clear preference for water in which the pH ranged from 7.8 to 8.2.

Figure 3:
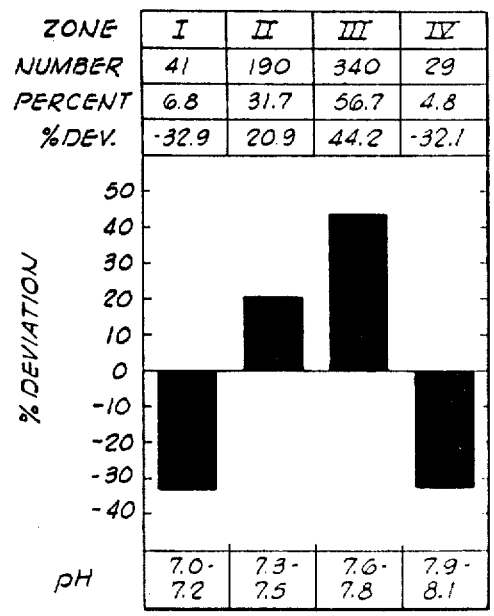

In order to more narrowly define the preferred pH range of the Largemouth Bass, the test represented by FIG. 3 was conducted. Again the oxygen content, temperature and dissolved solids were held are constant levels through the four zones. This time the fish showed a marked preference for Zones II and III, which had a pH range of 7.3 to 7.5 and 7.6 to 7.8, respectively.

In another experiment carried out in a controlled aquatic environment of the type described, and again using the Largemouth Bass species, both the dissolved oxygen content and the pH were varied from zone to zone while maintaining the temperature of the water and the dissolved solids content at constant levels. After permitting one hour for equilibration and achievement of steady state in the several zones, and allowing adequate time for response by the specimens, the specimens located within the several zones were counted, and the results of the tests are graphically set forth in FIG. 4 of the drawings. The data here plotted clearly show that the specimens preferred that zone in which the dissolved oxygen content was from 4.2 to 5.1 and the pH was from 7.2 to 7.5. It will be noted in referring to the graphed data the the higher, slightly alkaline pH appeared to clearly override the normally preferred dissolved oxygen content, as shown in FIG. 1 (in the range of from 6.9 to 8.2), in that only seven specimens remained in the zone having the preferred oxygen content of 7.2 to 8.3 but concurrently having a slightly acid pH of 6.4 to 6.6.

In the next test, represented by FIG. 5, the pH and temperature were varied while the dissolved oxygen and dissolved solids were held constant. The fish showed a clear preference for Zone IV in which the pH varied from 7.6 to 8.1 and in which the temperature varied from 82° F. to 88° F. It was earlier pointed out that the most desirable temperature range for bass is from 65° to 75° F. It is most significant here that the fish chose to locate themselves in the zone having the preferred pH even though the temperature in that zone was substantially above their preferred temperature.

Finally, in the test represented by FIG. 6, only the dissolved solids were held constant, while temperature, dissolved oxygen and pH were varied. The fish showed a high preference for Zone I, which had a temperature range from 54° to 57° F., a dissolved oxygen range from 3.9 to 4.2 ppm and a pH range from 7.5 to 7.9. Again, it is most significant to note that the fish chose the zone having preferred pH even though that zone had the combination of an undesirably low temperature and an undesirably low dissolved oxygen concentration.

The tests represented by FIGS. 1-6 are typical examples of a great many tests which I conducted. They serve to illustrate the significant result of all the tests, which is the determination the pH is an extremely influential water parameter with respect to the migratory tendencies of at least the fish species tested. Similar tests were conducted on the *Morone saxatilis,* commonly known as the Striped Bass, with very similar results.

Additionally, various field tests have been conducted under natural conditions, and those tests have verified the results shown in the laboratory tests. Typical field testing comprises observing the number of bass present within a zone of a lake while monitoring the various water parameters within that zone. The number of bass observed over a specified period of time is correlated with the water parameters during that time period. As the water parameters change, the number of bass observed per unit time also changes. Although such data is inherently more difficult to obtain and analyze due to the fact that the water parameters cannot be changed at will, a number of such observations have been made, and their general tendency is to verify the preferred pH range of bass which was determined in the laboratory, and to verify the determination that pH is a more influential parameter on the migratory tendency of bass than is temperature, dissolved oxygen, dissolved solids, or any combination of those three parameters.

In sum, I have determined that the tolerable pH range of the species of bass investigated is from pH 6.5 to about pH 9.6. Within this broad range of tolerance, I have determined that the preferred range of the Largemouth Bass is from about pH 7.5 to about pH 7.8, and that the preferred pH range of the Striped Bass is from about pH 7.5 to about pH 8.0. It has also been determined that these species of fish will locate themselves in an environment having their preferred pH range, even when that environment has undesirable values of salinity, dissolved oxygen concentration and temperature. That is, the effect of the pH upon the location of bass within a body of water is more pronounced than the combined effects of salinity, dissolved oxygen concentration and temperature. As a result of this discovery, it is now possible to more effectively locate and catch these species of fish by locating those zones, within the body of water being fished, having the desired pH.

If the pH were constant throughout a body of water, then, of course, the location of the species of fish, whether bass or other species, would be determined by some parameter other than pH. I have further determined, however, that the general situation within lakes, ponds, rivers and streams is that the pH varies widely within such bodies of water. The general situation is that the pH varies from point to point upon the surface of a body of water; and at any point on or within a body of water, pH varies with the time of day and the season of the year.

The implications of my determinations are very significant. First, to the long recognized effect of such water parameters as temperature upon the behavior of the fish can now be added the knowledge that the water acidity or basicity is extremely influential with respect to the migratory tendencies of at least these fish species, and it can be surmised that this particular parameter is, in all probability, of substantial influence with respect to other aquatic organisms—particularly species of fish. With this recognition, I have preceived the possibility of enhancing and improving the success with which otherwise conventional fish catching techniques and methodology can be utilized for locating and catching the species of bass investigated, and, with similar pre-investigation, other species of freshwater aquatic organisms, particularly fish. To this end, I have devised certain fish locating and catching methodology as well as apparatus to be used in the carrying out of such methodology. Such methods and apparatus are hereinafter described.

Another very important implication of the results of my investigations is the use of the knowledge based on such results in improving the efficiency and success with which commercial fish farming or raising operations can be carried out. Various species of fish, including the particular two investigated, are raised in numerous fish hatcheries around the United States for the purpose of stocking natural streams, as well as artificial ponds, lakes and the like. By carefully controlling the environment with specific reference to the pH parameter, the conditions for optimum growth can be more effectively realized, and the reduced gain in poundage due to hyperactivity in migrating from zone to zone under the influence of an uncontrolled pH gradient can be eliminated. Thus, an important aspect of the present invention is the proposal of an improved method for the raising of various fish species.

Prior to describing, in greater detail, the steps which are performed or carried out in practicing the fish locating and catching methods of the present invention, it is believed that such description will be more meaningful and better understood if a novel apparatus which I have conceived and developed for carrying out the method is initially described.

Referring to FIG. 7 of the drawings, one embodiment of the apparatus is generally designated by the numeral 10. The apparatus 10 includes a pH sensing device 12, which, in the form illustrated, is an extendable probe for contacting the water. The sensing device 12 can either be attached to an aquatic craft 14 by clamp means 16, or it can be extended or lowered and retracted relative to the craft by means of a reel 18 and an elongated electrical lead 20 wound upon the reel. The elongated lead 20 is connected at one end to the sensing device 12, and at the other end to a conventional rotating electrical contact 22 connected to the reel 18. The sensing device 12 is extended and retracted relative to the craft 14 by winding the lead 20 upon the reel 18. The rotation of the reel 18 is achieved by means of a conventional electric motor 24. In some forms of the structure, a hand crank can be employed.

On the lead 20 are numerous depth markings 26. There is a mark 26 every five feet along the lead so that the depth of the probe 12 in the water can be easily determined.

Also connected to the rotating electrical contact 22 is a second electrical lead 28. The electrical lead 28 is also connected to a pH display meter generally designated by the numeral 30. The display meter 30 is a means for displaying the pH sensed by the pH sensing device 12, and for indicating the relative closeness of that pH to the preferred pH range of certain species of fish. The display meter 30 has a scale 32, a pointer 34, and a preferred pH range indicator 36. The scale 32, in conjunction with the pointer 34, is used to indicate the pH of the water sensed by the sensing device 12. The preferred pH range indicator 36 comprises scale indicia 38 upon the display meter 30, which show that the preferred pH range of the *Micropterus salmoides*, commonly known as the Largemouth Bass, is the range of pH 7.5 to pH 7.8, and other scale indicia 40 showing that the preferred pH range of the *Morone saxatilis*, commonly known as the Striped Bass, is the range of pH 7.5 to pH 8.0.

The aquatic craft 14 is an open fishing boat having an outboard motor 42 mounted on the stern 44, and having the pH display meter 30 disposed in the boat between the gunwales 46 and 48, and forward of the stern 44. The pH display meter 30 is mounted along with other water parameter indicating instrumentation 50 so that all of the water parameter information can be readily assimilated and compared to determine those locations within a body of water where fish are most likely to be found and caught.

In the operation of the apparatus 10, the sensing device 12 is placed in contact with the water at random or selected locations after the boat 14 has been propelled to the vicinity of such locations by the motor 42. An electrical signal is transmitted from the sensing device 12 to the display meter 30 by means of the elongated electrical lead 20, the rotating electrical contact 22, and the second electrical lead 28. The signal so transmitted then causes the pointer 34 to indicate upon the scale 32 of the display meter 30, the pH of the water. The preferred pH range indicator 36 is superimposed upon the scale 32 so that, in conjunction with the scale 32 and the pointer 34, it indicates the relative closeness of the pH of the water to the preferred pH ranges of the Largemouth Bass and the Striped Bass. The Largemouth Bass and Striped Bass will generally be located within or very near those zones of the body of water which have a pH closest to the preferred pH ranges unless external disturbances have caused a temporary migration of the fish from these zones. These fish can therefore usually be caught in those same areas of the body of water more successfully than in other areas.

It will be readily apparent to those skilled in the art that the signal from the sensing device 12 to the display meter 30 can be conveyed by means other than the electrical leads 20 and 28. For example, in more sophisticated and expensive embodiments of the invention, the signal can also be transmitted pneumatically or by radio signal. Moreover, the display meter 30 can also be replaced by other display means, such as a digital readout of pH. Also, the preferred pH range indicator 36 can be replaced by a visual indicating light, or an audio indicating buzzer which would indicate the relative closeness of the water pH to the preferred pH ranges.

In another and very important aspect, the present invention relates, as previously indicated, to methods for locating, catching and raising aquatic organisms, and particularly certain species of freshwater game fish. Such aquatic organisms may be located and caught by the employment of apparatus similiar to that described. In order to most successfully apply these methods and apparatus to the task of locating and catching aquatic organisms by locating those areas having preferred values of certain environmental parameters, it is first necessary to determine the preferred range of the parameters for the species being sought, and this can be accomplished in the manner previously described if these parameters are not already known.

In using the described apparatus for carrying out the fish locating and catching method of the invention, the pH sensing device 12 is transported to a plurality of locations upon a body of water by means of the aquatic craft 14. The pH sensing device 12 is placed in contact with the water at those locations. The sensing device 12 may be kept in constant contact with the water slightly below the surface by attaching the sensing device to the craft 14 by means of the clamp 16. The sensing device 12 can be extended or lowered into the water and retrieved therefrom by means of the reel 18 and the elongated lead 20.

After placing the sensing device 12 in contact with the water, the pH of the water is measured and recorded. The pH is measured by means of the pH sensing device, and it is recorded by means of the pH display meter 30. The pH recorded on the display meter 30 is compared to the preferred pH range of the species being sought. Referring to FIG. 8, this comparison is made by means of the preferred pH range indicator 36 in conjunction with the scale 32 and the pointer 34. The preferred pH range indicator 36 comprises markings 38 upon the display meter 30, which show that the preferred pH range of the *Micropterus salmoides*, commonly known as the Largemouth Bass, is in the range of pH 7.5 to pH 7.8, and markings 40 showing that the preferred pH range of the *Morone saxatilis*, commonly known as the Striped Bass, is in the range of pH 7.5 to pH 8.0.

A signal generated by the sensing device 12 is transmitted to the display meter 30 by means of the elongated electrical lead 20, the rotating electrical contact 22, and the second electrical lead 28. This signal causes the pointer 34 to move relative to the scale 34 and the preferred pH range indicator 36. The pH of the water is indicated by the location of the pointer 34 upon the scale 32. The pointer 34 also indicates whether or not the pH of the water is within the preferred pH range of either the Largemouth Bass or the Striped Bass. Those species of fishes will then probably be found in those zones of water for which the pH is within the preferred pH range, and can then be caught at these locations by placing conventional fish catching means (tackle) in contact with the water. If no zones are found which have a pH within the preferred range, then the species may most likely be located and caught in zones having a pH nearest to the preferred pH range.

Based upon the positive effect upon the growth and reproduction of a species of aquatic organisms which results from their being located in an environment having a pH within the preferred range of the species, I have also invented improved methods for raising aquatic organisms. These methods are comprised of determining the pH of the water by placing conventional pH measuring means in contact with the water and then regulating the pH of the water to maintain it within the preferred pH range of the species. To most successfully raise the Largemouth Bass, the pH should be maintained within the range of pH 7.5 to pH 7.8. To raise the Striped Bass, the pH should be maintained within the range of pH 7.5 to pH 8.0.

What is claimed is:

1. An apparatus for locating within a body of fresh water an aquatic environment with a pH within a predetermined range preferred by Largemouth and Striped Bass fish which comprises:
   a surface aquatic craft for movement from one location to another on the surface of a body of water;
   pH sensing means mounted on the aquatic craft for contacting the water, said sensing means comprising:
      a pH sensing probe for sensing the pH of the water upon contact therewith; and
      means for extending and retracting the probe relative to the craft;
   means carried in the surface craft for indicating the pH sensed by the sensing means;
   means for transmitting a signal from the sensing means to the indicating means, including an electrical lead connecting the sensing means to the indicating means; and
   means in the craft in juxtaposition to said indicating means for sensibly portraying a range of pH values of from 7.5 to 8.0 corresponding to aquatic pH values characteristic of the aquatic pH preferred by bass, and facilitating immediate recognition of pH values within said range when they are indicated by said indicating means.

2. The apparatus of claim 1 wherein:
   the extending and retracting means is further characterized to comprise:
      an elongated second electrical lead attached at one end to the pH sensing probe;
      markings upon the elongated electrical lead to indicate the depth of the pH sensing probe beneath the water;
      a rotatable reel attached to the other end of the elongated electrical lead and also attached to the first electrical lead by means of a rotating electrical contact; and
      means for rotating the reel in either direction to extend or retract the pH sensing probe by winding the elongated electrical lead onto or paying it off the reel.

* * * * *